United States Patent [19]

Efendic

[11] Patent Number: 6,006,753
[45] Date of Patent: Dec. 28, 1999

[54] USE OF GLP-1 OR ANALOGS TO ABOLISH CATABOLIC CHANGES AFTER SURGERY

[75] Inventor: Suad Efendic, Lidingo, Sweden

[73] Assignee: Eli Lilly and Company, Indianapolis, Ind.

[21] Appl. No.: 08/916,991

[22] Filed: Aug. 21, 1997

[51] Int. Cl.$^6$ ................................................ A61B 19/00
[52] U.S. Cl. ................................ 128/898; 514/2; 514/3; 530/308
[58] Field of Search .................................... 128/897, 898; 514/772.3, 2, 3; 530/303, 308

[56] References Cited

U.S. PATENT DOCUMENTS

| | | | |
|---|---|---|---|
| 5,118,666 | 6/1992 | Habener | 514/12 |
| 5,120,712 | 6/1992 | Habener | 514/12 |
| 5,512,549 | 4/1996 | Chen et al. | 514/12 |
| 5,545,618 | 8/1996 | Buckley et al. | 514/12 |

FOREIGN PATENT DOCUMENTS

| | | |
|---|---|---|
| WO 95/05848 | 3/1995 | Sweden . |
| WO 96/29342 | 9/1996 | Sweden . |
| WO 91/11457 | 1/1991 | WIPO . |

OTHER PUBLICATIONS

J. Magnussun, B. Jeppsson, et al. "A Comparison of Enteral and Parenteral Glucose after Cholecystectomy", *Clinical Nutrition* (1987) 6: 117–119.

International Search Report for International Application No. PCT/US97/15042.

P. Kay Lund, Richard H. Goodman, Phillip C. Dee, and Joel F. Habener, "Pancreatic preproglucagon cDNA contains two glucagon–related coding sequences arranged in tandem," *Proc. Nat'l. Acad. Sci. USA*, vol. 79, pp. 345–349, Jan. 1982, Biochemistry.

Carolyn F. Deacon, Michael A. Nauck, Maibritt Toft–Nielsen, Lone Pridal, Berend Willms, and Jens J. Holst, "Both Subcutaneously and Intravenously Administered Glucagon–Like Peptide I Are Rapidly Degraded From the $NH_2$–Terminus in Type II Diabetic Patients and in Healthy Subjects," *Diabetes*, vol. 44, pp. 1126–1131, Sep. 1995.

Barry A. Mizock, "Alterations in Carbohydrate Metabolism During Stress: A review of the Literature," *The American Journal of Medicine*, vol. 98, pp. 75–84, Jan. 1995.

Mark Gutniak, Catherine Ørskov, Jens J. Holst, Bo Ahrén, and Suad Efendic, "Antidiabetogenic Effect of Glucagon–Like Peptide–1 (7–36)Amide In Normal Subjects And Patients With Diabetes Mellitus," *The New England Journal of Medicine*, pp. 1316–1322, May 14, 1992.

Abstract of M. Sachs, F. Asskali, H. Forster, E. Ungeheur, "[Postaggression metabolism following laparotomy and thoractomy] Untersuchungen uber den Postaggressionsstoffwechsel nach Laparotomien und Thoracotomien," *Chirurg*, p. 59, Jan. 1988.

Alberti, K., et al. (1980) Relative Role of Various Hormones in Metabolic Response to Injury, *Journal of Parenteral and Enteral Nutrition* 4(2): 141–146.

Alibegovic, A., et al. (1993) Pretreatment with Glucose Infusion Prevents Fatal Outcome After Hemorrhage in Food Deprived Rats, *Circulatory Shock* 39:1–6.

Black, P., et al. (1982) Mechanisms of Insulin Resistance Following Injury, *Ann. Surg.* 196(4):420–435.

Brandi, L., et al. (1990) Insulin resistance after surgery: normalization by insulin treatment, *Clinical Science* 79:443–450.

Brandi, L., et al. (1993) Insulin resistance of stress: sites and mechanisms, *Clinical Science* 85:525–535.

(List continued on next page.)

*Primary Examiner*—Mickey Yu
*Assistant Examiner*—Dinh X. Nguyen
*Attorney, Agent, or Firm*—Barnes & Thornburg

[57] ABSTRACT

This invention provides a method of attenuating post-surgical catabolic changes and hormonal responses to stress. GLP-1, a GLP-1 analog, or a GLP-1 derivative, is administered at a dose effective to normalize blood glucose.

13 Claims, 3 Drawing Sheets

OTHER PUBLICATIONS

Brooks, D., et al. (1986) Insulin Stimulates Branched Chain Amino Acid Uptake and Diminishes Nitrogen Flux from Skeletal Muscle of Injured Patients, *Journal of Surgical Research* 40:395–405.

Chernow, B., et al. (1987) Hormonal Responses to Graded Surgical Stress, *Arch Intern Med* 147:1273–1278.

Dhanvantari, S., et al. (1996) Role of Prohormone Convertases in the Tissue–Specific Processing of Proglucagon, *Molecular Endocrinology* 10(4):342–355.

Esahili, A., et al. (1991) Twenty–four Hour Fasting Increases Endotoxin Lethality in the Rat, *Eur J Surg* 157:89–95.

Fehmann, H. et al. (1992) At the Cutting Edge Glucagon–like peptide–1(7–37)/(7–36)amide is a new incretin, *Molecular and Cellular Endocrinology* 85:C39–C44.

Gelfand, R., et al. (1984) Role of Counterregulatory. Hormones in the Catabolic Response to Stress, *J.Clin. Invest.* 74:2238–2248.

Hammarqvist, F., et al. (1991) Biosynthetic Human Growth Hormone Preserves Both Muscle Protein Synthesis and the Decrease in Muscle–free Glutamine, and Improves Whole––body Nitrogen Economy After Operation, *Ann. Surg.* 216(2):184–191.

Hinton, P., et al. (1971) Insulin and Glucose to Reduce Catabolic Response to Injury in Burned Patients, *The Lancet* 767–769.

Nygren, J., et al. (1995) Preoperative Gastric Emptying Effects of Anxiety and Oral Carbohydrate Administration, *Annals of Surgery* 222(6):728–734.

Little, R., et al. (1987) Changes in Metabolic Control in Injury and Sepsis, *First Vienna Shock Forum* 463–475.

Ljungqvist, O., et al. (1994) Glucose Infusion Instead of Preoperative Fasting Reduces Postoperative Insulin Resistance, *J.Am. Coll. Surg.* 178:329–336.

Ljungqvist, O., et al. (1990) Food deprivation alters liver glycogen metabolism and endocrin responses to hemorrhage, *Am. J. Physiol.* 259 E692–E698.

Sakurai, Y., et al. (1995) Stimulation of Muscle Protein Synthesis by Long–Term Insulin Infusion in Severely Burned Patients *Annals of Surgery* 222(3):283–297.

Shaw, J., et al. (1987) An Integrated Analysis of Glucose, Fat, and Protein Metabolism in Severely Traumatized Patients, *Ann. Surg.* 209(1):63–72.

Splinter, W., et al. (1990) Unlimited Clear Fluid Ingestion Two Hours Before Surgery in Children Does Not Affect Volume of pH of Stomach Contents, *Anaesth Intens Care* 18:522–526.

Splinter, W., et al. (1991) Ingestion of Clear Fluids is Safe for Adolescents up to 3 H Before Anaesthesia, *British Journal of Anaesthesia* 66:48–52.

Thorell, A., et al. (1993) Development of Postoperative Insulin Resistance is Associated with the Magnitude of Operation, *Eur J Surg* 159:593–599.

Thorell, A., et al. (1996) Postoperative insulin resistance and circulating concentrations of stress hormones and cytokines, *Clinical Nutrition* 15:75–79.

Thorell, A., et al. (1994) Insulin resistance after abdominal surgery, *British Journal of Surgery* 81:59–63.

Wheeler, M., et al. (1993) Functional Expression of the Rat Glucagon–Like Peptide–I Receptor, Evidence for Coupling to both Adenylyl Cyclase and Phospholipase–C*, *Endocrinology* 133(1):57–62.

Wolffenbuttel, B., et al. (1995) Prevention of Complications in Non–Insulin–Dependent Diabetes Mellitus(NIDDM), *Drugs* 50(2): 263–288.

Woolfson, A., et al. (1979) Insulin to Inhibit Protein Catabolism After Injury, *The New England Journal of Medicine* 300(1):14–17.

Ziegler, T., et al. (1990) Use of Human Growth Hormone Combined with Nutritional Support in a Critical Care Unit, *Journal of Parenteral and Enteral Nutrition* 14(6):574–581.

Ziegler, T., (1994) Strategies for Attenuating Protein–Catabolic Responses in the Critically Ill, *Annu. Rev. Med.* 45:459–480.

USE OF GLP-1 OR ANALOGS TO ABOLISH CATABOLIC CHANGES AFTER SURGERY

BACKGROUND OF THE INVENTION

1. Field of the Invention

This invention relates to a method of improving recovery after surgery by preventing the catabolic reaction and insulin resistance caused by surgical trauma.

2. Background Information

Approximately 20–25,000 surgical treatments per million inhabitants are performed annually in the western world. Surgery, like any trauma, initiates marked changes in metabolism [Shaw, J. H. F., et al., *Ann. Surg.*, 209(1):63–72 (1989); Little, R. A., et al., *Prog. Clin. Biol. Res.* 263A:463–475 (1987); Frayn, K. N., *Clin. Endocrinol.* 24:577–599 (1986); Brandi, L., et al., *Clin. Sci.* 85:525–35 (1993)]. Accelerated synthesis of glucose, the primary fuel of tissue repair, is an important metabolic change after surgery, and occurs at the expense of body protein and energy stores [Gump, F. E., et al., *J. Trauma*, 14:378–88 (1974); Black, R. B., et al., *Ann. Surg.* 196:420–35 (1982)].

These changes have previously been attributed to the gluco-regulatory stress hormones and other catabolic factors, such as cytokines, that are released as a response to trauma. The more marked the change toward catabolism, the greater is the morbidity, and the slower is the recovery of the patient [Thorell, A., et al., *Eur. J. Surg.*, 159:593–99 (1993); Chernow, B., et al., *Arch. Intern. Med.*, 147:1273–8 (1987)].

Post-operative catabolic states may be treated with anabolic hormones, particularly, Growth Hormone and IGF-1 [Hammarkvist, F., et al., *Ann. Surg.*, 216(2):184–190 (1991); Ziegler, T., et al., *Annu. Rev. Med.*, 45:459–80 (1994); Ziegler, T. R., et al. *J. Parent. Ent. Nutr.* 14(6):574–81 (1990)]. Some studies show a clear benefit from insulin treatment in catabolic trauma patients [Hinton, P., et al., *Lancet*, 17(April):767–69 (1971); Shizgal, H., et al., *Am. J. Clin. Nutr.*, 50:1355–63 (1989); Woolfson, A. M. J., et al., *N. Clin. Nutr.*, 50:1355–63 (1989); Woolfson, A. M. J., et al., *N. Engl. J. Med.* 300:14–17 (1979); Brooks, D., et al., *J. Surg. Res.* 40:395–405 (1986); Sakurai; Y., et al., *Ann. Surg.* 222:283–97 (1995)].

Yet other studies, however, show that the post-operative benefits of insulin are often compromised by insulin resistance. In insulin resistance, normal concentrations of insulin elicit less than normal responses. Insulin resistance may be due to a decrease in binding of insulin to cell-surface receptors, or to alterations in intracellular metabolism. The first type, characterized as a decrease in insulin sensitivity, can typically be overcome by increased insulin concentration. The second type, characterized as a decrease in insulin responsiveness, cannot be overcome by large quantities of insulin.

Insulin resistance following trauma can be overcome by doses of insulin that are proportional to the degree of insulin resistance, and thus is apparently a decrease in insulin sensitivity [Brandi, L. S., et al., *Clin. Science* 79:443–450 (1990); Henderson, A. A., et al., *Clin. Sci.* 80:25–32 (1990)]. Reduction in insulin sensitivity following elective abdominal surgery lasts at least five days, but not more than three weeks, and is most profound on the first post-operative day, and may take up to three weeks to normalize [Thorell, A., et al., (1993)].

The causes of the observed transient insulin resistance following trauma are not well-understood. Both cortisol and glucagon may contribute to the catabolic response to trauma [Alberti, K. G. M. M., et al., *J. Parent. Ent. Nutr.* 4(2): 141–46 (1980); Gelfand, R. A., et al., *J. Clin. Invest.* 74(December):2238–2248 (1984); Marliss, E. B., et al., *J. Clin. Invest.* 49:2256–70 (1970)]. However, studies of post-operative insulin resistance has failed to show any correlation between changes in these catabolic hormones and changes in insulin sensitivity after surgery [Thorell, A., et al. (1993); Thorell A., *Karolinska Hospital and Institute*, 104 01 Stockholm, Sweden (1993); Thorell, A, et al., *Br. J. Surg.* 81:59–63 (1994)].

Increased availability of lipids after trauma may induce insulin resistance through the glucose-fatty acid cycle [Randle, P. J., et al., *Diab. Metab. Rev.* 4(7):623–38 (1988)].

Increased availability of free fatty acids (FFA) induced insulin resistance and changed substrate oxidation from glucose to fat, even in the presence of simultaneous infusions of insulin [Ferrannini, E., et al., *J. Clin. Invest.* 72:1737–47 (1983); Bevilacqua, S., et al., *Metabolism* 36:502–6 (1987); Bevilacqua, S., et al., *Diabetes* 39:383–89 (1990); Bonadonna, R. C., et al., *Am. J. Physiol.* 259:E736–50 (1990); Bonadonna, R. C., et al., *Am. J. Physiol.* 257:E49–56 (1989)].

Elective surgery is routinely performed after an 15 overnight fast to reduce risks of anesthesia. This entrenched practice of fasting the patient overnight (10–16 hours) before surgery enhances the development of the catabolic state, and worsens insulin resistance. Studies in rats undergoing stress, such as hemorrhage and endotoxemia, show that fasting for periods less than 24 hours markedly affects the catabolic response to trauma [Alibegovic, A., et al., *Circ. Shock*, 39:1–6 (1993); Eshali, A. H., et al. *Eur. J. Surg.*, 157:85–89 (1991); Ljungqvist, O., et al., *Am. J. Physiol.*, 22:E692–98 (1990)]. Even a short period of fasting before the onset of a trauma in rats markedly decreases carbohydrate reserves, profoundly changes the hormonal environment, increases stress response, and, most importantly, increases mortality [Alibegovic, A., et al., *Circ. Shock*, 39:1–6 (1993)].

Glucose administration before surgery, either orally [Nygren, J., et al., *Ann. Surg.* 222:728–34 (1995)], or by infusion, reduces insulin resistance after surgery, compared to fasted patients. Patients who received overnight glucose infusions (5 mg/kg/min) before elective abdominal surgery lost an average of 32% of insulin sensitivity after the operation, while patients, entering surgery after a routine overnight fast, lost an average of 55% of their insulin sensitivity [Ljungqvist, O., et al., *J. Am. Coll. Surg.* 178:329–36 (1994)].

In addition to the adverse effects of fasting on recovery from surgery, immobilization of the patient and hypocaloric nutrition during and after surgery also increase insulin resistance after surgery. In healthy subjects, 24 hours of immobilization and hypocaloric nutrition have been shown to induce a 20–30% increase in peripheral insulin resistance in healthy volunteers. Thus, postoperative insulin resistance previously reported after pre-operative glucose infusions [Ljungqvist, O., (1994)] may in part be due to the additive effects of post-operative bed rest and hypocaloric nutrition.

Given the prevalence of surgery, it is important to minimize negative side-effects, such as catabolic response and insulin resistance, in order to improve healing and to reduce mortality. Post-operative insulin resistance frustrates treatment of the catabolic state with insulin. The entrenched medical practice of pre-operative fasting exacerbates post-operative catabolic state and insulin resistance. Thus, a treatment that overcomes both the catabolic state and insulin resistance is needed.

As disclosed herein, one such treatment that overcomes both the catabolic state and insulin resistance is administration of glucose and insulin together before, during, and after the operation. Insulin infusion, however, creates the potential for hypoglycemia, which is defined as blood glucose below 0.3 mM. Hypoglycemia increases the risk of ventricular arrhythmia and is a dangerous consequence of insulin infusion. An algorithm for insulin infusion for diabetics was developed to prevent hypoglycemia [Hendra, T. J., et al., *Diabetes Res. Clin. Pract.,* 16:213–220 (1992)]. However, 21% of the patients developed hypoglycemia under this algorithm. In another study of glucose control following myocardial infarction, 18% of the patients developed hypoglycemia when infused with insulin and glucose [Malmberg, K. A., et al., *Diabetes Care,* 17:1007–1014 (1994)].

Insulin infusion also requires frequent monitoring of blood glucose levels so that the onset of hypoglycemia can be detected and remedied as soon as possible. In patients receiving insulin infusion in the cited study [Malmberg, 1994], blood glucose was measured at least every second hour, and the rate of infusion adjusted accordingly. Thus, the safety and efficacy of insulin-glucose infusion therapy for myocardial infarct patients depends on easy and rapid access to blood glucose data. Such an intense need for monitoring blood glucose places a heavy burden on health care professionals, and increases the inconvenience and cost of treatment. As a result, pre-surgical clinical care units often do not allot resources for monitoring and optimizing blood glucose levels before surgery, such as might be obtained by intravenous administration of insulin. Considering the risks and burdens inherent in insulin infusion, an alternate approach to pre/post-surgery control of catabolic reaction to trauma is needed.

The incretin hormone, glucagon-like peptide 1, abbreviated as GLP-1, is processed from proglucagon in the gut and enhances nutrient-induced insulin release [Krcymann B., et al., *Lancet* 2:1300–1303 (1987)]. Various truncated forms of GLP-1, are known to stimulate insulin secretion (insulinotropic action) and cAMP formation [see, e g., Mojsov, S., *Int. J. Peptide Protein Research,* 40:333–343 (1992)]. A relationship between various in vitro laboratory experiments and mammalian, especially human, insulinotropic responses to exogenous administration of GLP-1, GLP-1(7–36) amide, and GLP-1(7–37) acid has been established [see, e.g., Nauck, M. A., et al., *Diabetologia,* 36:741–744 (1993); Gutniak, M., et al., *New England J. of Medicine,* 326(20):1316–1322 (1992); Nauck, M. A., et al., *J. Clin. Invest.,* 91:301–307 (1993); and Thorens, B., et al., *Diabetes,* 42:1219–1225 (1993)]. GLP-1(7–36) amide exerts a pronounced antidiabetogenic effect in insulin-dependent diabetics by stimulating insulin sensitivity and by enhancing glucose-induced insulin release at physiological concentrations [Gutniak M., et al., *New England J. Med.* 326:1316–1322 (1992)]. When administered to non-insulin dependent diabetics, GLP-1(7–36) amide stimulates insulin release, lowers glucagon secretion, inhibits gastric emptying and enhances glucose utilization [Nauck, 1993; Gutniak, 1992; Nauck, 1993].

The use of GLP-1 type molecules for prolonged therapy has been obstructed because the serum half-life of such peptides is quite short. For example, GLP-1(7–37) has a serum half-life of only 3 to 5 minutes. GLP-1(7–36) amide has a half-life of about 50 minutes when administered subcutaneously. Thus, these GLP molecules must be administered as a continuous infusion to achieve a prolonged effect [Gutniak M., et al., *Diabetes Care* 17:1039–1044 (1994)]. In the present invention, GLP-1's short half-life and the consequent need for continuous administration are not disadvantages because the patient is typically hospitalized, before surgery, and fluids are continuously administered parenterally before, during, and after surgery.

SUMMARY OF THE INVENTION

The present invention therefore presents for the first time a method of attenuating post-surgical catabolic changes and insulin resistance, comprising, administering to a patient in need thereof a compound selected from the group consisting of GLP-1, GLP-1 analogs, GLP-1 derivatives, and pharmaceutically-acceptable salts thereof.

DETAILED DESCRIPTION OF THE INVENTION

Figure 1:
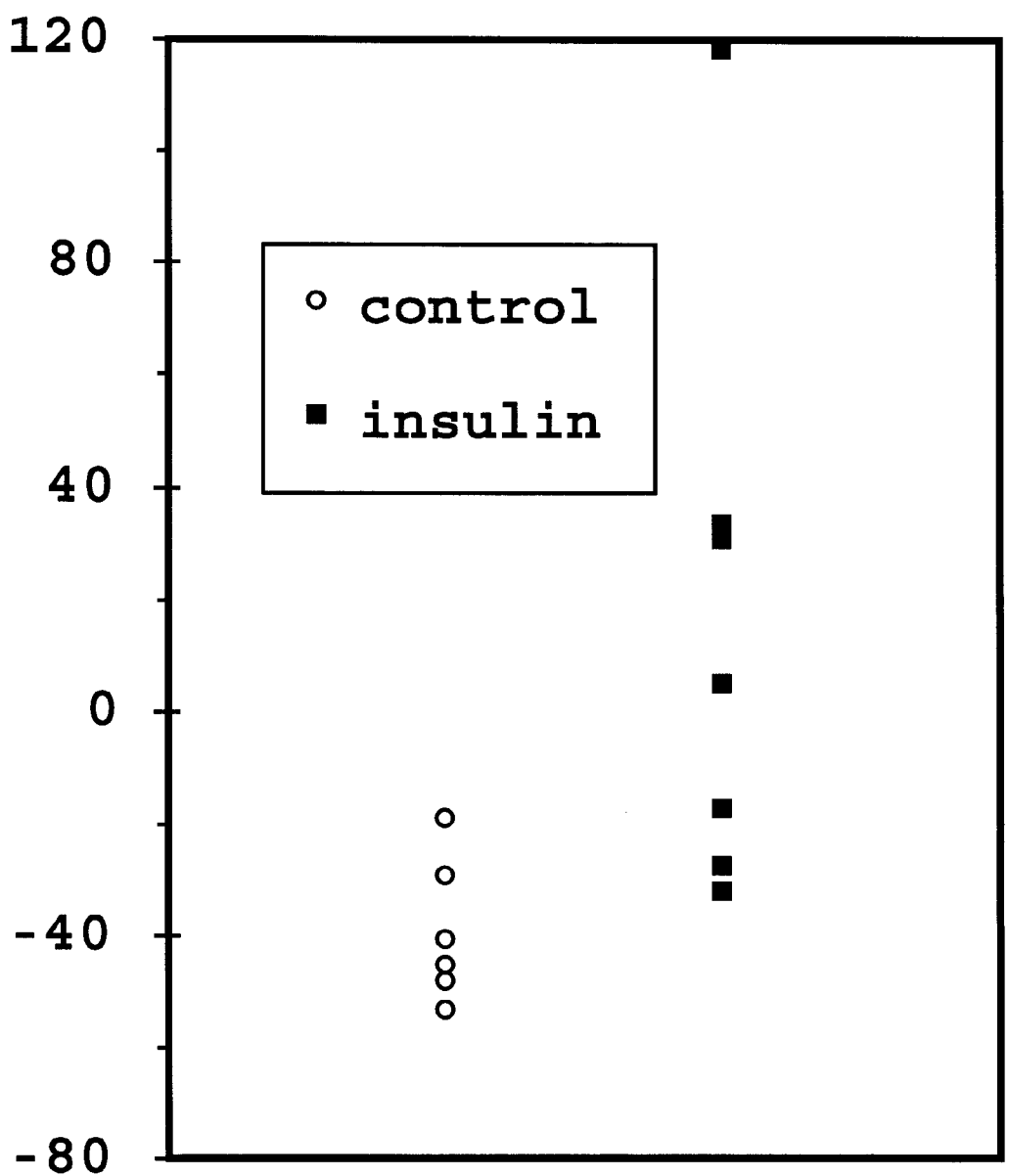
FIG. 1 is a graph of the percent change in glucose infusion rate (GIR) in the post-operative (postop) clamp period relative to the pre-operative (preop) clamp period for six (6) control patients (○) and seven (7) patients receiving a hyperinsulinemic, normoglycemic infusion (■) before and during elective surgery.

"GLP-1" means GLP-1(7–37). By custom in the art, the amino-terminus of GLP-1(7–37) has been assigned number 7 and the carboxy-terminus, number 37. The amino acid sequence of GLP-1(7–37) is well-known in the art, but is presented below for the reader's convenience:

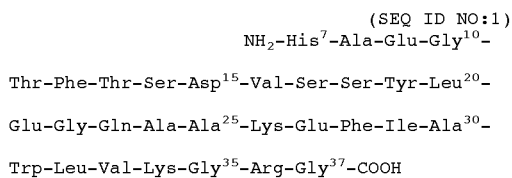

```
                                           (SEQ ID NO:1)
                  NH2-His7-Ala-Glu-Gly10-

Thr-Phe-Thr-Ser-Asp15-Val-Ser-Ser-Tyr-Leu20-

Glu-Gly-Gln-Ala-Ala25-Lys-Glu-Phe-Ile-Ala30-

Trp-Leu-Val-Lys-Gly35-Arg-Gly37-COOH
```

A "GLP-1 analog" is defined as a molecule having one or more amino acid substitutions, deletions, inversions, or additions compared with GLP-1. GLP-1 analogs known in the art include, for example, GLP-1(7–34) and GLP-1(7–35), GLP-1(7–36), Gln9-GLP-1(7–37), D-Gln9-GLP-1(7–37), Thr16-Lys18-GLP-1(7–37), and Lys18-GLP-1(7–37). Preferred GLP-1 analogs are GLP-1(7–34) and GLP-1(7–35), which are disclosed in U.S. Pat. No. 5,118,666, herein incorporated by reference, and also GLP-1(7–36), which are the biologically processed forms of GLP-1 having insulinotropic properties. Other GLP-1 analogs are disclosed in U.S. Pat. No. 5,545,618 which is incorporated herein by reference.

A "GLP-1 derivative" is defined as a molecule having the amino acid sequence of GLP-1 or of a GLP-1 analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Lower alkyl is $C_1$–$C_4$ alkyl. Furthermore, one or more side groups, or terminal groups, may be protected by protective groups known to the ordinarily-skilled protein chemist. The a-carbon of an amino acid may be mono- or dimethylated.

A preferred group of GLP-1 analogs and derivatives for use in the present invention is composed of molecules of the formula:

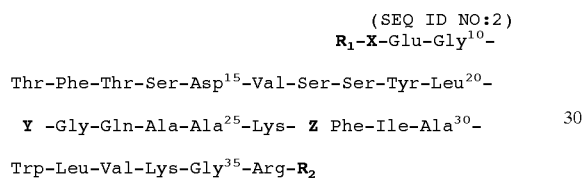

and the pharmaceutically-acceptable salts thereof, wherein: $R_1$ is selected from the group consisting of L-histidine, D-histidine, desamino-histidine, 2-amino-histidine, β-hydroxy-histidine, homohistidine, alpha-fluoromethyl-histidine, and alpha-methyl-histidine; X is selected from the group consisting of Ala, Gly, Val, Thr, Ile, and alpha-methyl-Ala; Y is selected from the group consisting of Glu, Gln, Ala, Thr, Ser, and Gly; Z is selected from the group consisting of Glu, Gln, Ala, Thr, Ser, and Gly; and $R_2$ is selected from the group consisting of $NH_2$ and Gly-OH; provided that the compound has an isoelectric point in the range from about 6.0 to about 9.0 and further providing that when $R_1$ is His, X is Ala, Y is Glu, and Z is Glu, $R_2$ must be $NH_2$.

Numerous GLP-1 analogs and derivatives having an isoelectric point in this range have been disclosed and include, for example:

GLP-1 (7-36)NH$_2$

Gly$^8$-GLP-1 (7-36)NH$_2$

Gln$^9$-GLP-1 (7-37)

D-Gln-$^9$-GLP-1 (7-37)

acetyl-Lys$^9$-GLP-1 (7-37)

Thr$^9$-GLP-1 (7-37)

D-Thr$^9$-GLP-1 (7-37)

Asn$^9$-GLP-1 (7-37)

D-Asn$^9$-GLP-1 (7-37)

Ser$^{22}$-Arg$^{23}$-Arg$^{24}$-Gln$^{26}$-GLP-1 (7-37)

Thr$^{16}$-Lys$^{18}$-GLP-1 (7-37)

Lys$^{18}$-GLP-1 (7-37)

Arg$^{23}$-GLP-1 (7-37)

Arg$^{24}$-GLP-1 (7-37), and the like

[see, e.g., WO 91/11457].

Another preferred group of active compounds for use in the present invention is disclosed in WO 91/11457, and consists essentially of GLP-1(7–34), GLP-1(7–35), GLP-1 (7–36), or GLP-1(7–37), or the amide form thereof, and pharmaceutically-acceptable salts thereof, having at least one modification selected from the group consisting of:

(a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;

(b) substitution of an oxidation-resistant amino acid for tryptophan at position 31;

(c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions is (a), (b), (d), and (e), the substituted amino acids can optionally be in the D-form and the amino acids substituted at position 7 can optionally be in the N-acylated or N-alkylated form.

Because the enzyme, dipeptidyl-peptidase IV (DPP IV), may be responsible for the observed rapid in vivo inactivation of administered GLP-1, [see, e.g., Mentlein, R., et al., *Eur. J. Biochem.*, 214:829–835 (1993)], administration of GLP-1 analogs and derivatives that are protected from the activity of DPP IV is preferred, and the administration of Gly$^8$-GLP-1(7–36)NH$_2$, Val$^8$-GLP-1(7–37)OH, a-methyl-Ala$^8$-GLP-1(7–36)NH$_2$, and Gly$^8$-Gln$^{21}$-GLP-1(7–37)OH, or pharmaceutically-acceptable salts thereof, is more preferred.

The use in the present invention of a molecule claimed in U.S. Pat. No. 5,188,666, which is expressly incorporated by reference, is preferred. Such molecule is selected from the group consisting of a peptide having the amino acid sequence:

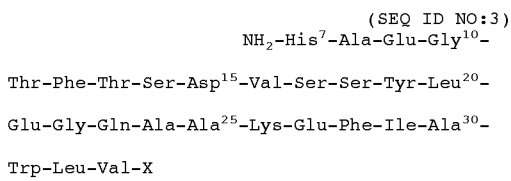

```
                                            (SEQ ID NO:3)
                            NH₂-His⁷-Ala-Glu-Gly¹⁰-

Thr-Phe-Thr-Ser-Asp¹⁵-Val-Ser-Ser-Tyr-Leu²⁰-

Glu-Gly-Gln-Ala-Ala²⁵-Lys-Glu-Phe-Ile-Ala³⁰-

Trp-Leu-Val-X
``` wherein X is selected from the group consisting of Lys and Lys-Gly; and a derivative of said peptide, wherein said peptide is selected from the group consisting of: a pharmaceutically-acceptable acid addition salt of said peptide; a pharmaceutically-acceptable carboxylate salt of said peptide; a pharmaceutically-acceptable lower alkylester of said peptide; and a pharmaceutically-acceptable amide of said peptide selected from the group consisting of amide, lower alkyl amide, and lower dialkyl amide.

Another preferred group of molecules for use in the present invention consists of compounds, claimed in U.S. Pat. No. 5,512,549, which is expressly incorporated herein by reference, of the general formula:

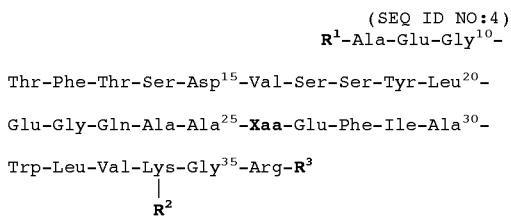

```
                                            (SEQ ID NO:4)
                            R¹-Ala-Glu-Gly¹⁰-

Thr-Phe-Thr-Ser-Asp¹⁵-Val-Ser-Ser-Tyr-Leu²⁰-

Glu-Gly-Gln-Ala-Ala²⁵-Xaa-Glu-Phe-Ile-Ala³⁰-

Trp-Leu-Val-Lys-Gly³⁵-Arg-R³
                      |
                      R²
``` and pharmaceutically-acceptable salts thereof, wherein $R^1$ is selected from the group consisting of 4-imidazopropionyl, 4-imidazoacetyl, or 4-imidazo-α,αdimethyl-acetyl; $R^2$ is selected from the group consisting of $C_6$–$C_{10}$ unbranched acyl, or is absent; $R^3$ is selected from the group consisting of Gly-OH or $NH_2$; and, Xaa is Lys or Arg, may be used in present invention.

More preferred compounds of SEQ ID NO:4 for use in the present invention are those in which Xaa is Arg and $R^2$ is $C_6$–$C_{10}$ unbranched acyl.

Highly preferred compounds of SEQ ID NO:4 for use in the present invention are those in which Xaa is Arg, $R^2$ is $C_6$–$C_{10}$ unbranched acyl, and $R^3$ is Gly-OH.

More highly preferred compounds of SEQ ID NO:4 for use in the present invention are those in which Xaa is Arg, $R^2$ is $C_6$–$C_{10}$ unbranched acyl, $R^3$ is Gly-OH, and $R^1$ is 4-imidazopropionyl.

The most preferred compound of SEQ ID NO:4 for use in the present invention is that in which Xaa is Arg, $R^2$ is $C_8$ unbranched acyl, $R^3$ is Gly-OH, and $R^1$ is 4-imidazopropionyl.

The use in the present invention of a molecule claimed in U.S. Pat. No. 5,120,712, which is expressly incorporated by reference, is highly preferred. Such molecule is selected from the group consisting of a peptide having the amino acid sequence:

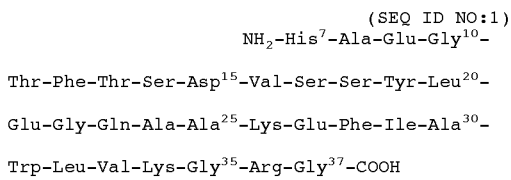

```
                                            (SEQ ID NO:1)
                            NH₂-His⁷-Ala-Glu-Gly¹⁰-

Thr-Phe-Thr-Ser-Asp¹⁵-Val-Ser-Ser-Tyr-Leu²⁰-

Glu-Gly-Gln-Ala-Ala²⁵-Lys-Glu-Phe-Ile-Ala³⁰-

Trp-Leu-Val-Lys-Gly³⁵-Arg-Gly³⁷-COOH
``` and a derivative of said peptide, wherein said peptide is selected from the group consisting of: a pharmaceutically-acceptable acid addition salt of said peptide; a pharmaceutically-acceptable carboxylate salt of said peptide; a pharmaceutically-acceptable lower alkylester of said peptide; and a pharmaceutically-acceptable amide of said peptide selected from the group consisting of amide, lower alkyl amide, and lower dialkyl amide.

The use of GLP-1(7–36) amide, or a pharmaceutically-acceptable salt thereof, in the present invention is most highly preferred. The amino acid sequence of GLP-1(7–36) amide is:

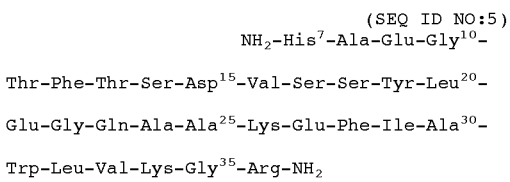

```
                                            (SEQ ID NO:5)
                            NH₂-His⁷-Ala-Glu-Gly¹⁰-

Thr-Phe-Thr-Ser-Asp¹⁵-Val-Ser-Ser-Tyr-Leu²⁰-

Glu-Gly-Gln-Ala-Ala²⁵-Lys-Glu-Phe-Ile-Ala³⁰-

Trp-Leu-Val-Lys-Gly³⁵-Arg-NH₂
```

Methods for preparing the active compound used in the present invention, namely, GLP-1, an GLP-1 analog, or a GLP-1 derivative used in the present invention are well-known, and are described in U.S. Pat. Nos. 5,118,666, 5,120,712, and 5,523,549, which are incorporated by reference.

The amino acid portion of the active compound used in the present invention, or a precursor thereto, is made either by 1) solid-phase synthetic chemistry; 2) purification of GLP molecules from natural sources; or 3) recombinant DNA technology.

Solid phase chemical synthesis of polypeptides is well known in the art and may be found in general texts in the area such as Dugas, H. and Penney, C., *Bioorganic Chemistry*, Springer-verlag, N.Y. (1981), pp. 54–92, Merrifield, J. M., *Chem. Soc.*, 85:2149 (1962), and Stewart and Young, *Solid Phase Peptide Synthesis*, Freeman, San Francisco (1969) pp. 24–66.

For example, the amino acid portion may be synthesized by solid-phase methodology utilizing a 430A peptide synthesizer (PE-Applied Biosystems, Inc., 850 Lincoln Center Drive, Foster City, Calif. 94404) and synthesis cycles supplied by PE-Applied Biosystems. BOC-amino acids and other reagents are commercially available from PE-Applied Biosystems and other chemical supply houses. Sequential Boc chemistry using double couple protocols are applied to the starting p-methyl benzhydryl amine resins for the production of C-terminal carboxamides. For the production of C-terminal acids, the corresponding PAM resin is used. Asn, Gln, and Arg are coupled using preformed hydroxy benzotriazole esters. The following side chain protecting groups may be used:

Arg, Tosyl
Asp, cyclohexyl
Glu, cyclohexyl
Ser, Benzyl
Thr, Benzyl
Tyr, 4-bromo carbobenzoxy Boc deprotection may be accomplished with trifluoroacetic acid in methylene chloride. Following completion of the synthesis the peptides may be deprotected and cleaved from the resin with anhydrous hydrogen fluoride (HF) containing 10% meta-cresol. Cleavage of the side chain protecting group(s) and of the peptide from the resin is carried out at −5° C. to 5° C., preferably on ice for 60 minutes. After removal of the HF, the peptide/resin is washed with ether, and the peptide extracted with glacial acetic acid and lyophilized.

Techniques well-known to the ordinarily-skilled artisan in recombinant DNA technology may be used to prepare the active compound used in present invention. In fact, recombinant DNA methods may be preferable because of higher yield. The basic steps in recombinant production are:

a) isolating a natural DNA sequence encoding a GLP-1 molecule or constructing a synthetic or semi-synthetic DNA coding sequence for a GLP-1 molecule, b) placing the coding sequence into an expression vector in a manner suitable for expressing proteins either alone or as a fusion proteins, c) transforming an appropriate eukaryotic or prokaryotic host cell with the expression vector, d) culturing the transformed host cell under conditions that will permit expression of a GLP-1 molecule, and e) recovering and purifying the recombinantly produced GLP-1 molecule.

As previously stated, the coding sequences may be wholly synthetic or the result of modifications to the larger, native glucagon-encoding DNA. A DNA sequence that encodes preproglucagon is presented in Lund, et al., *Proc. Natl. Acad. Sci. U.S.A.* 79:345–349 (1982) and may be used as starting material in the semisynthetic production of the compounds of the present invention by altering the native sequence to achieve the desired results.

Synthetic genes, the in vitro or in vivo transcription and translation of which results in the production of a GLP-1 molecule, may be constructed by techniques well known in the art. Owing to the natural degeneracy of the genetic code, the skilled artisan will recognize that a sizable yet definite number of DNA sequences may be constructed, all of which encode GLP-1 molecules.

The methodology of synthetic gene construction is well-known in the art. See Brown, et al. (1979) *Methods in Enzymology,* Academic Press, N.Y., 68:109–151. The DNA sequence is designed from the desired amino acid sequence using the genetic code, which is easily ascertained by the ordinarily-skilled biologist. Once designed, the sequence itself may be generated using conventional DNA synthesizing apparatus such as the Model 380A or 380B DNA synthesizers (PE-Applied Biosystems, Inc., 850 Lincoln Center Drive, Foster City, Calif. 94404).

To express the amino acid portion of a compound used in the present invention, one inserts the engineered synthetic DNA sequence in any one of many appropriate recombinant DNA expression vectors through the use of appropriate restriction endonucleases. See generally Maniatis et al. (1989) *Molecular Cloning; A Laboratory Manual,* Cold Springs Harbor Laboratory Press, N.Y., Vol. 1–3. Restriction endonuclease cleavage sites are engineered into either end of the GLP-1 molecule-encoding DNA to facilitate isolation from, and integration into, amplification and expression vectors well-known in the art. The particular endonucleases employed will be dictated by the restriction endonuclease cleavage pattern of the parent expression vector employed. Restriction sites are chosen to properly orient the coding sequence with control sequences, thereby achieving proper in-frame reading and expression of the protein of interest. The coding sequence must be positioned to be in proper reading frame with the promoter and ribosome binding site of the expression vector, both of which are functional in the host cell in which the protein is to be expressed.

To achieve efficient transcription of the synthetic gene, it must be operably associated with a promoter-operator region. Therefore, the promoter-operator region of the synthetic gene is placed in the same sequential orientation with respect to the ATG start codon of the synthetic gene.

A variety of expression vectors useful for transforming prokaryotic and eukaryotic cells are well known in the art. See *The Promega Biological Research Products Catalogue* (1992) (Promega Corp., 2800 Woods Hollow Road, Madison, Wis., 53711–5399); and *The Stratagene Cloning Systems Catalogue* (1992) (Stratagene Corp., 11011 North Torrey Pines Road, La Jolla, Calif., 92037). Also, U.S. Pat. No. 4,710,473 describes circular DNA plasmid transformation vectors useful for expression of exogenous genes in *E. coli* at high levels.

These plasmids are useful as transformation vectors in recombinant DNA procedures and (a) confer on the plasmid the capacity for autonomous replication in a host cell;

(b) control autonomous plasmid replication in relation to the temperature at which host cell cultures are maintained;

(c) stabilize maintenance of the plasmid in host cell populations;

(d) direct synthesis of a protein product indicative of plasmid maintenance in a host cell population;

(e) provide in-series restriction endonuclease recognition sites unique to the plasmid; and (f) terminate mRNA transcription.

These circular DNA plasmids are useful as vectors in recombinant DNA procedures for securing high levels of expression of exogenous genes.

Having constructed an expression vector for the amino acid portion of a compound used in the present invention, the next step is to place the vector into a suitable cell and thereby construct a recombinant host cell useful for expressing the polypeptide. Techniques for transforming cells with recombinant DNA vectors are well known in the art and may be found in such general references as Maniatis, et al. *supra.* Host cells made be constructed from either eukaryotic or prokaryotic cells.

Prokaryotic host cells generally produce the protein at higher rates and are easier to culture. Proteins expressed in high-level bacterial expression systems characteristically aggregate in granules or inclusion bodies, which contain high levels of the overexpressed protein. Such protein aggregates typically must be recovered, solubilized, denatured and refolded using techniques well known in the art. See Kreuger, et al. (1990) in *Protein Folding, Gierasch and King, eds.,* pgs 136–142, American Association for the Advancement of Science Publication No. 89–18S, Washington, D.C.; and U.S. Pat. No. 4,923,967.

Alterations to a precursor GLP-1 or GLP-1 analog amino acid sequence, to produce a desired GLP-1 analog or GLP-1 derivative, are made by well-known methods: chemical modification, enzymatic modification, or a combination of chemical and enzymatic modification of GLP-1 precursors. The techniques of classical solution phase methods and semi-synthetic methods may also be useful for preparing the GLP-1 molecules used in the present invention. Methods for preparing the GLP-1 molecules of the present invention are well known to an ordinarily skilled peptide chemist.

Addition of an acyl group to the epsilon amino group of $Lys^{34}$ may be accomplished using any one of a variety of methods known in the art. See *Bioconjugate Chem.* "Chemical Modifications of Proteins: History and Applications" pages 1, 2–12 (1990) and Hashimoto et al., *Pharmacuetical Res.* 6(2):171–176 (1989).

For example, an N-hydroxy-succinimide ester of octanoic acid can be added to the lysyl-epsilon amine using 50% acetonitrile in borate buffer. The peptide can be acylated either before or after the imidazolic group is added. Moreover, if the peptide is prepared recombinantly, acylation prior to enzymatic cleavage is possible. Also, the lysine in the GLP-1 derivative can be acylated as taught in WO96-29342, which is incorporated herein by reference.

The existence and preparation of a multitude of protected, unprotected, and partially-protected, natural and unnatural, functional analogs and derivatives of GLP-1 (7–36)amide and GLP-1 (7–37) molecules have been described in the art [see, e.g., U.S. Pat. No. 5,120,712 and 5,118,666, which are herein incorporated by reference, and Orskov, C., et al., *J. Biol. Chem.*, 264(22):12826–12829 (1989) and WO 91/11457 (Buckley, D. I., et al., published Aug. 8, 1991)].

Optionally, the amino and carboxy terminal amino acid residues of GLP-1 derivatives may be protected, or, optionally, only one of the termini is protected. Reactions for the formation and removal of such protecting groups are described in standard works including, for example, "Protective Groups in Organic Chemistry", Plenum Press, London and New York (1973); Green, T. H., "Protective Groups in Organic Synthesis", Wiley, N.Y. (1981); and "The Peptides", Vol. I, Schröder and Lübke, Academic Press London and New York (1965). Representative amino-protecting groups include, for example, formyl, acetyl, isopropyl, butoxycarbonyl, fluorenylmethoxycarbonyl, carbobenzyloxy, and the like. Representative carboxy-protecting groups include, for example, benzyl ester, methyl ester, ethyl ester, t-butyl ester, p-nitro phenyl ester, and the like.

Carboxy-terminal, lower-alkyl-ester, GLP-1 derivatives used in the present invention are prepared by reacting the desired ($C_1$–$C_4$) alkanol with the desired polypeptide in the presence of a catalytic acid such as hydrochloric acid. Appropriate conditions for such alkyl ester formation include a reaction temperature of about 50° C. and reaction time of about 1 hour to about 3 hours. Similarly, alkyl ester derivatives of the Asp and/or Glu residues can be formed.

Preparation of a carboxamide derivative of a compound used in the present invention is formed, for example, as described in Stewart, J. M., et al., *Solid Phase Peptide Synthesis*, Pierce Chemical Company Press, 1984.

A pharmaceutically-acceptable salt form of GLP-1, of a GLP-1 analog, or of a GLP-1 derivative may be used in the present invention. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like. Preferred acid addition salts are those formed with mineral acids such as hydrochloric acid and hydrobromic acid, and, especially, hydrochloric acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like. The salt forms are particularly preferred.

A GLP-1, GLP-1 analog, or GLP-1 derivative used in the present invention may be formulated with one or more excipients before use in the present invention. For example, the active compound used in the present invention may be complexed with a divalent metal cation by well-known methods. Such metal cations include, for example, $Zn^{++}$, $Mn^{++}$, $Fe^{++}$, $Co^{++}$, $Cd^{++}$, $Ni^{++}$, and the like.

Optionally, the active compound used in the present invention may be combined with a pharmaceutically-acceptable buffer, and the pH adjusted to provide acceptable stability, and a pH acceptable for parenteral administration.

Optionally, one or more pharmaceutically-acceptable anti-microbial agents may be added. Meta-cresol and phenol are preferred pharmaceutically-acceptable anti-microbial agents. One or more pharmaceutically-acceptable salts may be added to adjust the ionic strength or tonicity. One or more excipients may be added to further adjust the isotonicity of the formulation. Glycerin is an example of an isotonicity-adjusting excipient.

Administration may be via any route known to be effective by the physician of ordinary skill. Parenteral administration is preferred. Parenteral administration is commonly understood in the medical literature as the injection of a dosage form into the body by a sterile syringe or some other mechanical device such as an infusion pump. Parenteral routes include intravenous, intramuscular, subcutaneous, intraperitoneal, intraspinal, intrathecal, inracerebroventricular, intraarterial, subarachnoid, and epidural. Intravenous, intramuscular, and subcutaneous routes of administration of the compounds used in the present invention are more preferred. Intravenous and subcutaneous routes of administration of the compounds used in the present invention are yet more highly preferred. For parenteral administration, an active compound used in the present invention preferably is combined with distilled water at an appropriate pH.

Additional pharmaceutical methods may be employed to control the duration of action. Controlled release preparations may be achieved by the use of polymers to complex or absorb the active compound used in the present invention. Extended duration may be obtained by selecting appropriate macromolecules, for example, polyesters, polyamino acids, polyvinylpyrrolidone, ethylenevinyl acetate, methylcellulose, carboxymethylcellulose, or protamine sulfate, and by selecting the concentration of macromolecules, as well as the methods of incorporation, in order to prolong release. Another possible method to extend the duration of action by controlled release preparations is to incorporate an active compound used in the present invention into particles of a polymeric material such as polyesters, polyamino acids, hydrogels, poly (lactic acid) or ethylene vinylacetate copolymers. Alternatively, instead of incorporating a compound into these polymeric particles, it is possible to entrap a compound used in the present invention in microcapsules prepared, for example, by coacervation techniques or by interfacial polymerization, for example, hydroxymethylcellulose or gelatin-microcapsules, respectively, or in colloidal drug delivery systems, for example, liposomes, albumin microspheres, microemulsions, nanoparticles, and nanocapsules, or in macroemulsions. Such teachings are disclosed in Remington's Pharmaceutical Sciences (1980).

According to the teachings of this invention, a patient is in need of the compounds used in the present invention for about 1–16 hours before surgery is performed on said patient, during surgery on said patient, and after said patient's surgery for a period of not more than about 5 days.

As mentioned above, the length of time before surgery to begin to administer the compounds used in the present invention is from about sixteen hours to about one hour before surgery begins. The length of time before surgery when the compounds used in the present invention should be administered in order to reduce catabolic effects and insulin resistance will depend on factors whose effects are known to the physician of ordinary skill, and include, most importantly, whether the patient is fasted or supplied with a glucose infusion or beverage, or some other form of sustenance during the preparatory period before surgery, and also, without limitation, the patient's sex, weight and age, the severity of any inability to regulate blood glucose, the underlying causes of any inability to regulate blood glucose, the expected severity of the trauma caused by the surgery, the route of administration and bioavailability, the persistence in the body, the formulation, and the potency of the compound administered. A preferred time interval within which to begin administration of the compounds used in the present invention is from about one hour to about ten hours before surgery begins. The most preferred interval to begin administration is between two hours and eight hours before surgery begins.

As explained hereinabove, insulin resistance following a particular type of surgery, elective abdominal surgery, is most profound on the first post-operative day, lasts at least five days, and may take up to three weeks to normalize [Thorell, A., et al., (1993)]. Thus, the post-operative patient may be in need of administration of the compounds used in the present invention for a period of time following the trauma of surgery that will depend on factors that the physician of ordinary skill will comprehend and determine. Among these factors are whether the patient is fasted or supplied with a glucose infusion or beverage, or some other form of sustenance following surgery, and also, without limitation, the patient's sex, weight and age, the severity of any inability to regulate blood glucose, the underlying causes of any inability to regulate blood glucose, the actual severity of the trauma caused by the surgery, the route of administration and bioavailability, the persistence in the body, the formulation, and the potency of the compound administered. The preferred duration of administration of the compounds used in the present invention is not more than five days following surgery.

The term "post-surgical catabolic changes" is well-known to the surgeon of ordinary skill [Shaw, J. H. F., et al., Ann. Surg. (1989); Little, R. A., et al. (1987); Frayn, K. N. (1986); Brandi, L., et al., (1993)], and is defined herein as a state of metabolism caused by the trauma of surgery that may be characterized by one or more of the following phenomena: negative nitrogen balance, with loss of body nitrogen [Wernerman, J., et al., J. Parent. Enter. Nutr. 10:578–82 (1986); Tashiro, T., et al., J. Parent. Enter. Nutr. 9:452–5 (1985)], peripheral utilization of fat in preference to glucose with reduction of the respiratory quotient [Frayn, K. N., et al., Arch. Emerg. Med. 4:91–9 (1987); Stjernstrom, H., et al., Clin. Physiol. 1:59–72 (1981)], and endogenous glucose production at the expense of body protein and energy stores in spite of hyperglycemia [Gump, F. E., et al., (1974); Black, R. B., et al., (1982); Frayn, K. N., et al., (1987); Frayn, K. N. Br. Med. Bull. 41(3):232–9 (1985)].

The term "insulin resistance" is also well-known to physicians of ordinary skill, and is defined herein as a physiological condition wherein normal concentrations of insulin elicit less than normal responses. Insulin resistance may be due to a decrease in binding of insulin to cell-surface receptors, or to alterations in intracellular metabolism. The first type, characterized as a decrease in insulin sensitivity, can typically be overcome by increased insulin concentration. The second type, characterized as a decrease in insulin responsiveness, cannot be overcome by large quantities of insulin. Insulin resistance following trauma can be overcome by doses of insulin that are proportional to the degree of insulin resistance, and thus is apparently caused by a decrease in insulin sensitivity [Brandi, L.S., et al., Clin. Science 79:443–450 (1990); Henderson, A. A., et al., Clin. Sci. 80:25–32 (1990)]. Reduction in insulin sensitivity following elective abdominal surgery lasts at least five days, but not more than three weeks, and is most profound on the first post-operative day, and may take up to three weeks to normalize [Thorell, A., et al., (1993)]. The causes of the observed transient insulin resistance following trauma are not well-understood.

The dose of GLP-1, GLP-1 analog, or GLP-1 derivative effective to normalize a patient's blood glucose level will depend on a number of factors, among which are included, without limitation, the patient's sex, weight and age, the severity of inability to regulate blood glucose, the underlying causes of inability to regulate blood glucose, whether glucose, or another carbohydrate source, is simultaneously administered, the route of administration and bioavailability, the persistence in the body, the formulation, and the potency. Where administration is continuous, a suitable dosage rate is between 0.25 and 6 pmol/kg body weight/min, preferably from about 0.5 to about 1.2 pmol/kg/min. Where administration is intermittent, the dose per administration should take into account the interval between doses, the bioavailability of GLP-1, GLP-1 analog, or GLP-1 derivative, and the level needed to effect normal blood glucose. It is within the skill of the ordinary physician to titrate the dose and rate of administration of GLP-1, GLP-1 analog, or GLP-1 derivative to achieve the desired clinical result.

The present invention will be more readily understood by reference to specific examples, which are provided to illustrate, not to limit, the present invention.

EXAMPLE 1

Thirteen patients, scheduled for elective orthopedic surgery (hipartroplasty), participated in the study. None of the patients had any history or signs of metabolic disease, liver affection, or diabetes mellitus. Fasting blood glucose levels, CRP and liver tests (bilirubine, alkaline phosfatase, AST and ALT) were normal in all thirteen patients.

Seven patients (insulin group, age, 56±5 years; BMI, 25±1 kg/m$^2$) were studied beginning at 08:00 after an overnight fast. After an initial basal period, during which time samples were taken for measurements of blood glucose and hormones, and indirect calorimetry was performed for 30 min, insulin (Actrapid®, Novo, Copenhagen) was infused intravenously at a constant rate of 0.8 mU/kg/min, while a variable intravenous infusion of glucose (200 mg/ml) was given to maintain blood glucose at a constant level (4.5 mM). After one hour at steady state conditions, all patients underwent a standardized surgical treatment (hipartroplasty). The operation started 290±23 minutes after the beginning of insulin infusion. The hyperinsulinemic, normoglycemic clamp was then maintained during surgery and continued for a further 3–4 hours after surgery. The data will be presented according to the following nomenclature:

| | |
|---|---|
| basal | 30 min. before start of insulin infusion |
| preop clamp | steady state hyperinsulinemic, normoglycemic clamp for 60 min before surgery |
| early op | from 10 to 40 min. after the initiation of surgery |
| late op | the last 30 min. of surgery |
| postop clamp | steady state hyperinsulininemic, normoglycemic clamp for 60 min., starting 143 ± 30 min after the initiation of surgery. |

A second group of patients (control group, n=6, age, 59±3 years; BMI, 26±1 kg/m$^2$), matched to the insulin group with regard to age and BMI, received the same preoperative protocol (basal and preop clamp) seven days before surgery. The control group received no basal or preop clamp on the day of surgery. However, immediately surgery, each patient in the control group received infusion of insulin (0.8 mU/kg/min.), and a hyperinsulinemic, normoglycemic (4.5 mM) clamp (postop) was begun.

Indirect calorimetry (Deltatrac® Dansjöö, Sweden) [Frayn, K. N. *J. Appl. Physiol.* 55(2):628–34 (1983); Takala, J., et al., *Crit. Care Med.* 17(10): 1041–47 (1989)] was performed for 30 minutes during the basal phase, twice during surgery (early op and late op), and during the last 30 minutes of the preop and postop clamps. Timed sampling of urine for analysis of urinary urea excretion was performed. After correction for changes in urea pool size [Tappy, L, et al., *Diabetes* 37:1212–16 (1988)], non-protein energy expenditure (EE), respiratory quotients (RQ) and substrate oxidation rates were calculated.

Blood samples were collected from a heated hand vein repeatedly during the basal, preop, early op, late op and postop periods. Blood glucose was measured immediately upon collection using the glucose oxidase method (Yellow Springs Instruments, Yellow Springs, Ohio) [Hugget, A. S., et al., *Lancet* 2:368–70 (1957)]. Radio immunoassays (RIA) were used to measure serum concentrations of insulin [Grill, V., et al., *Metabolism* 39:251–58 (1990)]; C-peptide (Novo Research, Bagsvaerd, Denmark); cortisol [Harris, V., et al., In Jaffe, B.M. & Behrman, H.R., eds. Methods of hormone *radioimmunoassay*, Academic Press, New York and London (1979) pp. 643–56]; and glucagon (Euro-Diagnostica AB, Malm6, Sweden) [Faloona, G. R., et al., *Glucagpn radioimmunoassay technique.* 5 Vol. 1: Academic Press, New York (1974)].

All values are individual values, or mean+SEM (standard error of the mean). Statistical significance is accepted at p<0.05 using Wilcoxon's signed rank test and the Mann-Whitney U-test for paired and unpaired data respectively. Because serum insulin levels at the postop clamp tended to be lower in the control group compared to the insulin group (p=0.06), GIR during clamps were also corrected to the prevailing insulin levels by dividing GIR and the mean serum insulin level during the 60 minute steady-state periods.

Serum insulin levels were similar between the two groups, both at basal and during the preop clamp. In the insulin group, insulin levels remained around 60 μU/ml during surgery and the postop clamp. In the control group, insulin levels remained unchanged compared to basal levels during surgery. Insulin levels at the postop clamp in the control group were not significantly different from the levels during the preop clamp nor different to those in the insulin group during the postop clamp.

C-peptide levels (Table I) were similar between the groups at basal and during the preop and postop clamps. The insulin group displayed lower C-peptide levels during surgery compared to the control group.

Serum glucagon levels decreased (p<0.05) after surgery in both groups (Table I). However, the relative change after surgery (% vs preop) was higher in the insulin group (p<0.01 vs control).

Serum cortisol levels (Table I) decreased after surgery in the insulin group while levels in the control group tended to increase (p=0.1). The postoperative levels of cortisol were lower in the insulin group compared to the control group (p<0.05).

TABLE I

Hormone levels in patients undergoing hipartroplasty after an overnight fast (control, n = 6), or after four hours of physiological hyperinsulinemia (insulin, n = 7).

| | basal | pre op | early op | late op | post op |
|---|---|---|---|---|---|
| C-peptide | | | | | |
| control | .68 ± .08 | .41 ± .09 | .70 ± .11 | .70 ± .13 | .31 ± .09 |
| insulin | .68 ± .09 | .45 ± .05 | .42 ±.06† | .58 ± .12 | .52 ± .11 |
| Glucagon | | | | | |
| control | 48 ± 2 | 42 ± 1 | 43 ± 3 | 41 ± 3 | 37 ± 2* |
| insulin | 58 ± 7 | 52 ± 3† | 40 ± 3 | 35 ± 4 | 33 ± 4* |
| Cortisol | | | | | |
| control | 229 ± 39 | 238 ± 21 | 154 ± 63 | 116 ± 43 | 366 ± 83* |
| insulin | 171 ± 41 | 266 ± 35 | 234 ± 46 | 212 ± 44 | 172 ± 83†* |

*p < 0.05 compared to preop by the Wilcoxon signed rank test;
†p < 0.05 compared to control by the Mann-Whitney U-test.

Glucagon levels decreased in both groups after surgery although the greatest reduction (%) was found in the insulin group (p<0.01 vs control). Cortisol levels decreased after surgery in the insulin group (p<0.05 vs preop), while levels in the control group tended to increase (p=0.1). Thus, cortisol levels were significantly lower in the insulin group compared to the control group after surgery (p<0.05).

Glucose infusion rates (GIRs) were not significantly different between the insulin and control groups during the preop clamp. The control group had a decreased average GIR required to maintain normoglycemia during the postop clamp compared to the preop clamp (−39±5%, p<0.05). In contrast, the insulin group maintained the GIR during surgery, and, on average, even tended to increase GIR in the postop clamp (+16±20%, p=0.2). Most significantly, and unexpectedly, the average GIR during the postop clamp in the insulin group was significantly higher compared to the control group (p<0.05) (see FIG. 1). All changes in GIR at the preop and postop clamps were statistically significant (p<0.05), regardless of whether GIR was corrected for the mean serum insulin levels during the periods of steady state.

Glucose and fat oxidation rates were similar between the groups before surgery. During surgery, glucose oxidation rates were significantly higher, while fat oxidation rates were significantly lower in the insulin group (p<0.05 vs. control). At the postop clamp, no change in substrate oxidation rates could be found in the insulin group as compared to the preop clamp. Resting energy expenditure (EE) did not differ between the groups during or after surgery, and remained the same in both groups after surgery as compared to the preop clamp.

Fasting glucose levels were similar between the insulin and control groups. At steady-state during insulin infusion, normoglycemia was maintained, resulting in mean intra-individual coefficients of variation for glucose of 4.6% in the control, and 6.2% in the insulin group.

These findings conclusively demonstrate that patients undergoing elective surgery in the fasted state develop postoperative insulin resistance and increased fat oxidation. Furthermore, these findings also demonstrate for the first time that catabolic changes after surgery are completely abolished, and the hormonal response to stress completely attenuated, if the patients enter surgical stress in a state of elevated insulin levels which is maintained throughout the operation.

EXAMPLE 2

Figure 2:
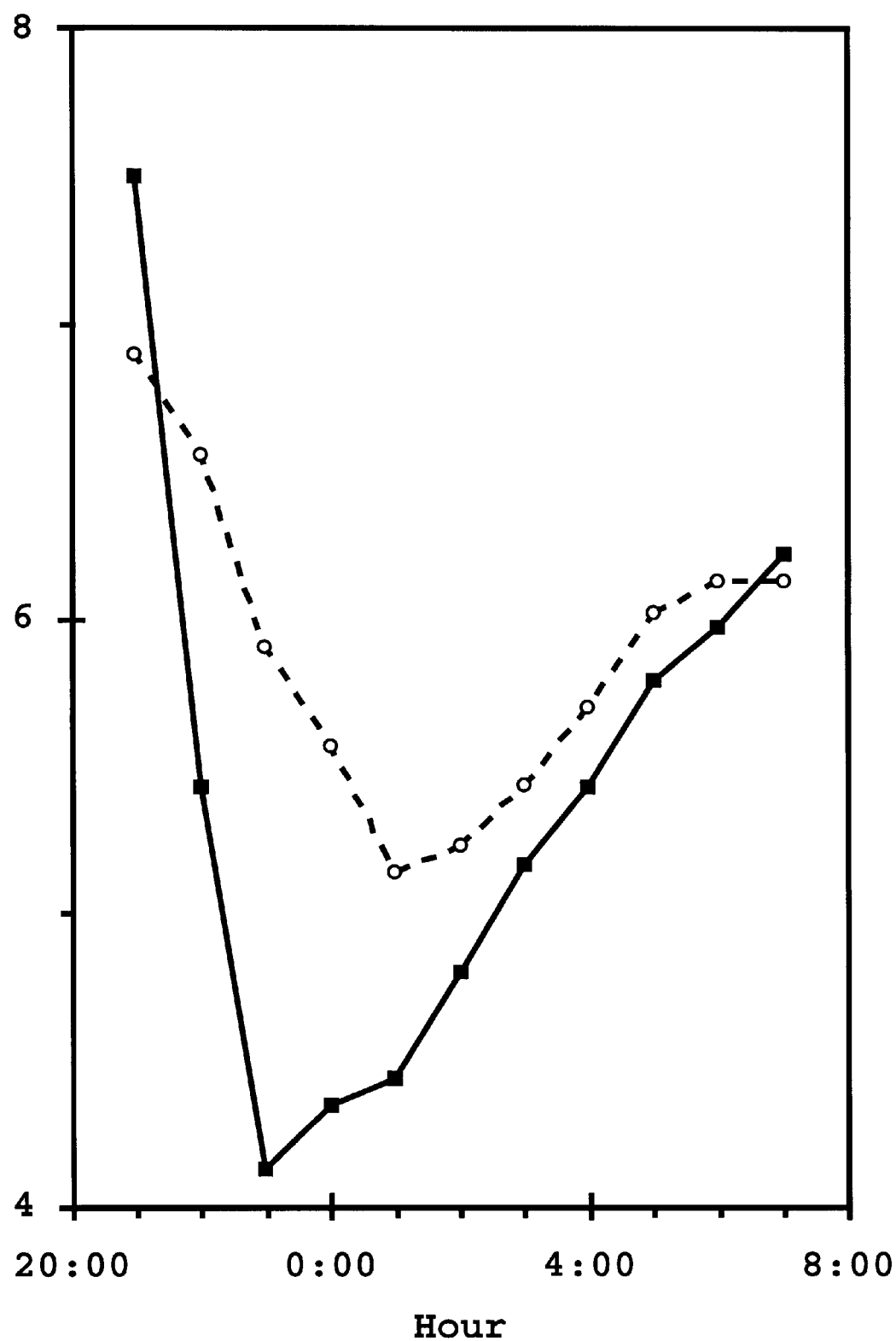
FIG. 2 is a graph showing the effect of continuous infusion GLP-1 (7–36) amide on average blood glucose concentration (mM) (─■─) in five non-insulin dependent diabetes mellitus (NIDDM) patients during the night. The graph also depicts the effect of continuous insulin infusion on average blood glucose concentration (─○─) in the same five NIDDM patients, but on a different night.

GLP-1 (7–36) amide was administered by a subcutaneous infusion at a dose rate of 1.2 pmol/kg/hr, for ten hours during the night, to five patients having non-insulin dependent diabetes (NIDDM). As a control, insulin was continuously infused in the same five patients, but on a different day than the GLP-1 (7–36) amide infusion. The rate of insulin infusion was adjusted every two hours to achieve optimum control, and to avoid hypoglycemia. As demonstrated 35 by the data in Table II, and in FIG. 2, subcutaneous infusion of GLP-1 (7–36) amide nearly normalized blood glucose without inducing hypoglycemia in any of the patients. The metabolic control with GLP-1 (7–36) amide was better than that achieved by insulin, and the average blood glucose level was lower for GLP-1 (7–36) amide treatment than for the control by a statistically significant amount at 23:00, 0:00, and at 1:00.

TABLE II

Average blood glucose levels for five NIDDM patients continuously infused for ten hours during the night with GLP-1 (7–36) amide. In a control study with the same patients on a different day, insulin was administered by continuous infusion.

| | GLP-1 Infusion | | Insulin Infusion (Control) | |
|---|---|---|---|---|
| Hour | Average Blood Glucose (mM) | Std. Error (mM) | Average Blood Glucose (mM) | Std. Error (mM) |
| 21:00 | 7.5 | 0.45 | 6.9 | 0.68 |
| 22:00 | 5.4 | 0.76 | 6.6 | 0.55 |
| 23:00 | 4.1 | 0.16 | 5.9 | 0.98 |
| 0:00 | 4.4 | 0.23 | 5.6 | 0.90 |
| 1:00 | 4.4 | 0.29 | 5.1 | 0.58 |
| 2:00 | 4.8 | 0.34 | 5.2 | 0.58 |
| 3:00 | 5.2 | 0.41 | 5.4 | 0.30 |
| 4:00 | 5.4 | 0.41 | 5.7 | 0.25 |
| 5:00 | 5.8 | 0.41 | 6.0 | 0.30 |
| 6:00 | 6.0 | 0.45 | 6.1 | 0.38 |
| 7:00 | 6.2 | 0.45 | 6.1 | 0.33 |

EXAMPLE 3

Figure 3:
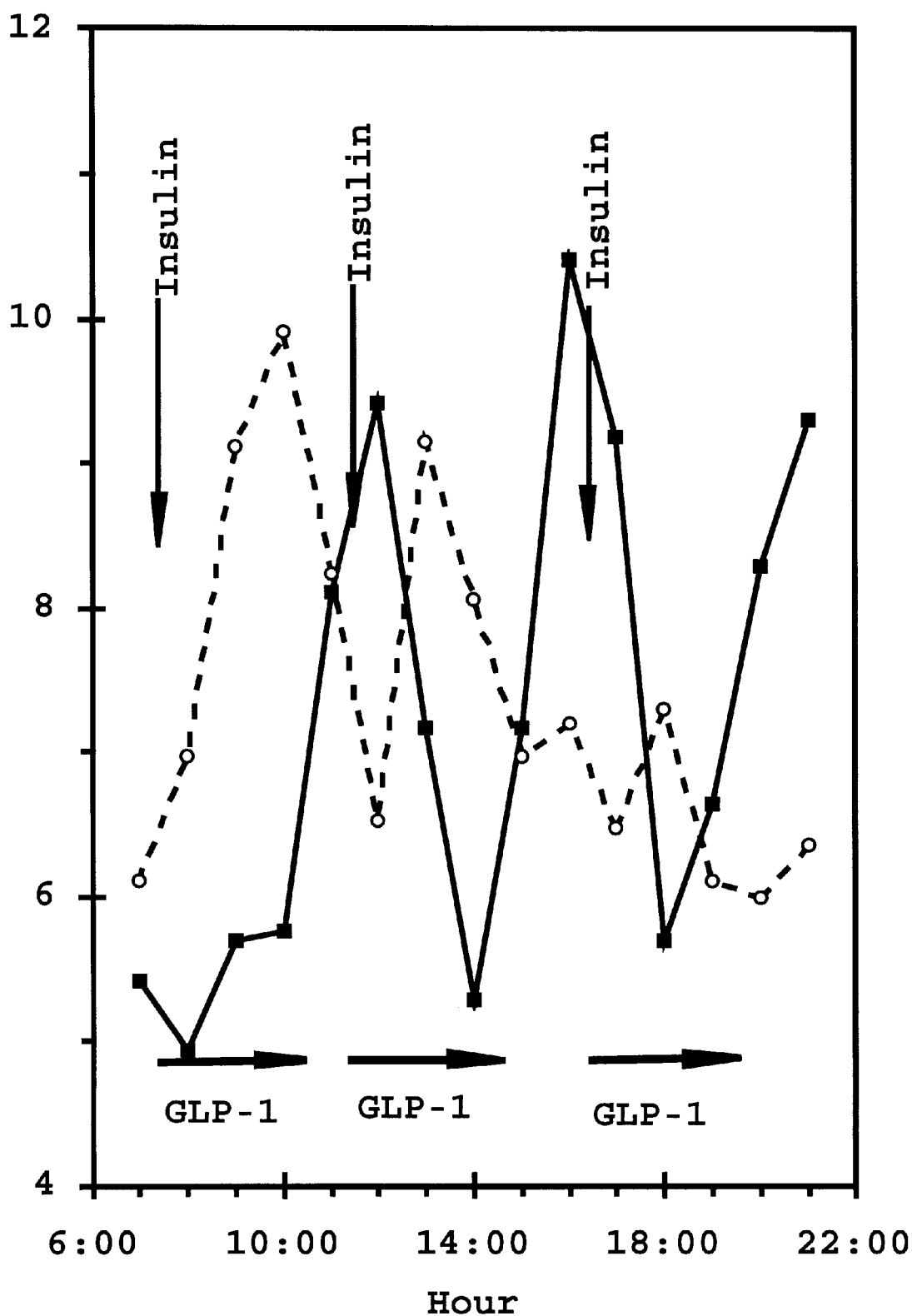
FIG. 3 is a graph showing the effect of GLP-1 (7–36) amide infusion on average blood glucose concentration (mM) (─■─) in five NIDDM patients when infused during the day, for three hours starting at the beginning of each of three meals. The graph also depicts the effect of subcutaneous injection of insulin on average blood glucose concentration (─○─) in the same five NIDDM patients, but on a different day, and with injection shortly before each meal.

During the day, GLP-1 (7–36) amide was infused into five NIDDM patients for three hours during breakfast, lunch, and dinner. The infusion times were 7:30–10:30 (breakfast), 10:30–1:30 (lunch), and 4:30–7:30 (dinner), as indicated in FIG. 3. In a control experiment in the same five NIDDM patients conducted on a different day, insulin was injected subcutaneously just before the start of the meals, as indicated in FIG. 3. While GLP-1 was infused, the post-prandial glucose excursions observed with insulin injection were eliminated, and normal blood glucose levels were maintained. Immediately after terminating each GLP-1 (7–36) amide infusion, the blood glucose level increased significantly. No untoward side effects of GLP-1 (7–36) amide were observed. These data indicate that GLP-1 (7–36) amide infusion more effectively controls post-prandial glucose levels than insulin injection, and that the control is effective as long as GLP-1 (7–36) amide infusion is continued.

TABLE III

Average blood glucose levels for five NIDDM patients infused with GLP-1 (7–36) amide for three hours, beginning at the start of each meal. In a control study with the same patients on a different day, insulin was administered by subcutaneous injection just before each meal. Meals began at 7:30, 10:30, and at 4:30.

| | GP-1 Infusion | | Insulin Subcutaneous Injection | |
|---|---|---|---|---|
| Hour | Average Blood Glucose (mM) | Std. Error (mM) | Average Blood Glucose (mM) | Std. Error (mM) |
| 7:00 | 5.4 | 0.35 | 6.1 | 0.41 |
| 8:00 | 4.9 | 0.38 | 7.0 | 0.51 |
| 9:00 | 5.7 | 0.59 | 9.1 | 0.74 |
| 10:00 | 5.8 | 1.06 | 9.9 | 0.78 |
| 11:00 | 8.1 | 0.94 | 8.2 | 0.76 |
| 12:00 | 9.4 | 0.59 | 6.5 | 0.74 |
| 13:00 | 7.2 | 1.18 | 9.1 | 0.90 |
| 14:00 | 5.3 | 1.21 | 8.1 | 0.91 |
| 15:00 | 7.2 | 0.71 | 7.0 | 0.87 |
| 16:00 | 10.4 | 0.26 | 7.2 | 0.57 |
| 17:00 | 9.2 | 1.06 | 6.5 | 0.59 |
| 18:00 | 5.7 | 1.59 | 7.3 | 0.65 |
| 19:00 | 6.6 | 0.94 | 6.1 | 0.59 |
| 20:00 | 8.3 | 0.71 | 6.0 | 0.41 |
| 21:00 | 9.3 | 0.71 | 6.4 | 0.44 |

I claim:

1. A method of attenuating post-surgical catabolic changes and insulin resistance, comprising, administering to a patient in need thereof a compound selected from the group consisting of GLP-1, GLP-1 analogs, GLP-1 derivatives, and pharmaceutically-acceptable salts thereof.

2. The method of claim 1, wherein the compound is administered intravenously.

3. The method of claim 1, wherein the compound is administered subcutaneously.

4. The method of claims 2 or 3, wherein the administration is continuous.

5. The method of claim 4 wherein the rate of administration of the compound is between 0.25 and 6 pmol/kg/min.

6. The method of claim 5 wherein the rate of administration of the compound is between 0.5 and 2.4 pmol/kg/min.

7. The method of claim 5 wherein said rate is between about 0.5 and about 1.2 pmol/kg/min.

8. The method of claim 2 wherein the intravenous administration is intermittent.

9. The method of claim 2 wherein the compound is administered intravenously and also administered by another parenteral route.

10. The method of claim 9 wherein the other parenteral route is the subcutaneous route.

11. The method of claim 1 wherein the compound administered is GLP(7–36) amide, or a pharmaceutically-acceptable salt thereof.

12. A method of attenuating post-surgical catabolic changes and hormonal responses to stress, comprising, administering to a patient in need thereof a compound that exerts insulinotropic activity by interacting with the same receptor, or receptors, with which GLP-1, GLP-1 analogs, and GLP-1 derivatives interact in exerting their insulinotropic activity.

13. A method of attenuating post-surgical catabolic changes and hormonal responses to stress, comprising, administering a compound that enhances insulin sensitivity by interacting with the same receptor, or receptors, with which GLP-1, GLP-1 analogs, and GLP-1 derivatives interact to enhance insulin sensitivity.

* * * * *

UNITED STATES PATENT AND TRADEMARK OFFICE
CERTIFICATE OF CORRECTION

PATENT NO.    : 6,006,753
DATED         : December 28, 1999
INVENTOR(S)   : Suad Efendic It is certified that error appears in the above-identified patent and that said Letters Patent is hereby corrected as shown below:

Column 1,
Line 4, insert the following paragraph before "BACKGROUND OF THE INVENTION", -- This application claims the benefit of U.S. Provisional Application Serial No. 60/024,982 filed August 30, 1996. --

Signed and Sealed this

Sixteenth Day of March, 2004

JON W. DUDAS
*Acting Director of the United States Patent and Trademark Office*